(12) United States Patent
Norris

(10) Patent No.: US 7,515,949 B2
(45) Date of Patent: Apr. 7, 2009

(54) WAVELET TRANSFORM OF A PLETHYSMOGRAPHIC SIGNAL

(75) Inventor: Mark A. Norris, Louisville, CO (US)

(73) Assignee: General Electric Company, Schenectady, NY (US)

( * ) Notice: Subject to any disclaimer, the term of this patent is extended or adjusted under 35 U.S.C. 154(b) by 699 days.

(21) Appl. No.: 11/170,181

(22) Filed: Jun. 29, 2005

(65) Prior Publication Data

US 2007/0004977 A1    Jan. 4, 2007

(51) Int. Cl.
*A61B 5/1455* (2006.01)

(52) U.S. Cl. .................. 600/336; 600/323; 702/189

(58) Field of Classification Search ............. 600/322, 600/323, 331; 702/189, 190, 191
See application file for complete search history.

(56) References Cited

U.S. PATENT DOCUMENTS

| 6,067,462 | A * | 5/2000 | Diab et al. ............. 600/310 |
| 6,094,592 | A | 7/2000 | Yorkey et al. ............. 600/475 |
| 6,263,222 | B1 | 7/2001 | Diab et al. ............. 600/310 |
| 6,393,311 | B1 | 5/2002 | Edgar, Jr. et al. ......... 600/323 |
| 6,519,486 | B1 | 2/2003 | Edgar, Jr. et al. ......... 600/336 |
| 6,650,917 | B2 | 11/2003 | Diab et al. ............. 600/323 |
| 6,810,277 | B2 | 10/2004 | Edgar, Jr. et al. ......... 600/336 |
| 2004/0039273 | A1 * | 2/2004 | Terry ..................... 600/322 |

FOREIGN PATENT DOCUMENTS

WO    WO 03/000125    *    1/2003

* cited by examiner

*Primary Examiner*—Eric F Winakur
*Assistant Examiner*—Etsub D Berhanu
(74) *Attorney, Agent, or Firm*—Marsh Fischmann & Breyfogle LLP

(57) ABSTRACT

A photoplethysmographic system and method is provided for filtering a photoplethysmographic (pleth) signal to reduce the effects of noise in the signal. The system and method utilize a combination of frequency, time and/or magnitude information, to identify and separate transient signal components within a pleth signal from repeating signal components within the pleth signal. Typically, signal components of interest repeat over a period that corresponds with a patient's heartbeat. Such periodically repeating signals may be identified as stationary signals/objects within a frequency and time-based analysis. In contrast, motion artifacts or other sources of noise are often isolated (i.e., non-repeating) transient events and may be identified as non-stationary objects in a frequency and time-based analysis. Data associated with identified transient events may be filtered from or otherwise removed from a given signal. In this regard, a pleth signal may be cleansed prior to its use for, e.g., blood analyte determinations.

36 Claims, 14 Drawing Sheets

WAVELET TRANSFORM OF A PLETHYSMOGRAPHIC SIGNAL

FIELD OF THE INVENTION

The present invention relates generally to photoplethysmography and, in particular, to filtering a photoplethysmographic signal so as to reduce the effects of noise in the signal.

BACKGROUND OF THE INVENTION

Pulse oximeters determine an oxygen saturation level of a patient's blood, or related analyte values, based on transmission/absorption characteristics of light transmitted through or reflected from a patient's tissue. In particular, pulse oximeters generally include a probe for attaching to a patient's appendage such as a finger, earlobe or nasal septum. The probe is used to transmit pulsed optical signals of at least two wavelengths, typically red and infrared, through the patient's appendage. The transmitted signals are received by a detector that provides an analog electrical output signal representative of the received optical signals. By processing the electrical signal and analyzing signal values for each of the wavelengths at different portions of the patient's pulse cycle (i.e., pulsatile signal), information can be obtained regarding blood oxygen saturation and/or other parameter values such as pulse rate, or blood pressure/blood volume related values.

Extraction of patient physiological conditions from the plethysmographic signals can be quite effective using a well positioned sensor and when the patient or subject is resting. However, motion artifacts can easily swamp the desired information (i.e., the signal of interest) included in the plethysmographic signals when the patient is moving around and/or performing muscular contractions. Other sources of artifact or 'noise' that can occlude the signal of interest in a plethysmographic signal include power line noise, electrical noise from other medical equipment and light contamination. Some artifacts can severely impair the signals, whereas other types can be filtered out or do not significantly effect the desired information included in the plethysmographic signals. Furthermore, depending upon the severity and type of artifacts present in the plethysmographic signals, some techniques for extracting the desired patient physiological conditions may not be appropriate and alternative techniques may need to be employed.

Filtering techniques including low pass, band pass, and high pass filtering can be used to remove noise signal components from the signal of interest where the noise signal component occupies a frequency range outside the signal of interest. More sophisticated techniques for conventional noise filtering include multiple notch filters, which are suitable for use where the noise signal component exists at multiple, distinct frequencies, all outside the frequency band of the signal of interest.

The pass band(s) of such filters are often set in relation to a fundamental frequency of the plethysmographic signal. Generally, this fundamental frequency corresponds to the heart rate of the patient. The fundamental frequency is sometimes determined by performing a Fourier transform on the time-based plethysmographic signal to generate a frequency spectrum of the signal. As may be appreciated, in the frequency spectrum, periodic signals such as a heart rate are represented as spectral peaks. Often, noise is randomly dispersed across the spectrum such that the fundamental may be determined. However, in high motion conditions, the noise signal may overwhelm the periodic signal of the heart such that the fundamental cannot be effectively determined by simple Fourier analysis.

Further, it is often the case that the frequency spectrum of the noise signal components overlaps the frequency spectrum of the signal of interest such that even if a fundamental frequency of the plethysmographic signal could be determined, high levels of artifact/noise co-exist within the frequency band of interest. That is, some sources of noise may include frequency components in the frequency band of interest. In such cases, conventional filtering techniques based solely on frequency information may be ineffective in extracting the signal of interest from noise signals.

SUMMARY

The inventor has recognized that while frequency analysis is generally a powerful tool for analyzing the components of a time-based signal that repeats on a periodic basis (e.g., a stationary signal), such analysis is often less useful when a signal includes non-stationary events which do not repeat within a sample region. For instance, Fourier transforming a signal in the time domain (e.g., a signal sampled at a predetermined frequency) results in a signal that represents the frequency components of the original signal. Events that repeat within the signal are generally represented as peaks in a frequency spectrum. However, isolated non-repeating events (i.e., transient events) may not be represented within the frequency spectrum. Accordingly, in instances where non-periodic motion artifact or other artifact exists within the signal it may be difficult to effectively separate signal components of interest from artifact components based solely on frequency based information. Accordingly, the inventor has recognized that use of a combination of frequency, time and/or magnitude information may provide for enhanced identification and/or isolation of signal components from a pleth signal.

By utilizing a combination of frequency, time and/or magnitude information, the inventor has determined that it is possible to effectively identify and separate transient signal components within a pleth signal from stationary signal components within the pleth signal (e.g., signal components of interest which repeats within a given time window of the signal). In the case of pleth signals, the signal components of interest typically repeat over a period that corresponds with a patient's heartbeat. Such periodically repeating signals may be identified as stationary objects within a frequency and time-based analysis. In contrast, motion artifacts or other sources of noise are often isolated (i.e., non-repeating) transient events and may be identified as non-stationary objects in a frequency and time-based analysis. Furthermore, data associated with these transient events may be filtered from or otherwise removed from a given signal. In this regard, a pleth signal may be cleansed prior to its use for, e.g., blood analyte determinations.

In accordance with one aspect of the present invention, a method and apparatus (collectively "utility") is provided for removing transient events from a detector signal to generate a modified signal, which may be utilized to provide physiological patient data. In application of the utility, a series of time periods of a time-based signal reflective of one or more optical signals incident on a detector of a pulse oximeter are each transformed to generate a series of transformed signals having at least a frequency component. The series of time periods may be of equally spaced time durations (e.g., successive or overlapping) such that the resulting series of transformed signals are effectively indexed against time. The series of transformed signals may then be monitored to identify one or more frequency bands of one or more of the transformed signals which is potentially corrupted by artifact. Upon identifying such a frequency band within one or more of the series of transformed signals, this frequency band may be removed from a particular transformed signal to generate a modified transformed signal. In this regard, each individual transformed signal may be cleansed to remove one or more frequency bands that is potentially corrupted by artifact. Of note, such frequency bands may change between individual transformed signals. The series of transformed signals and/or modified transformed signals may then be used to generate physiological patient data.

In one arrangement, a modified time-based signal is generated from the series of transformed signals and/or modified transformed signals (e.g., through an inverse transform process). Accordingly, this modified time-based signal may be substantially free of data associated with a frequency band(s) at an individual time period that is determined to be corrupted by artifact.

The use of the individual transforms for each of the series of time periods allows for different frequency bands to be removed from different time periods of the pleth signal. In this regard, the utility is analogous to a nonlinear filter that is adapted to remove individual frequency bands from individual time periods of a time-based signal.

Identifying a frequency band that is potentially corrupted by noise may be performed by any appropriate manner. In one arrangement, individual peaks within each of the series of transformed signals may be compared to peaks in other transformed signals within a given time window to determine whether the peak is a stationary peak associated with repeating data (e.g., a signal component of interest) or a transient peak in a frequency and time domain. Accordingly, if a peak is determined to be transient (i.e., a non-repeating event) a frequency band associated with that transient peak for a given time period may be removed from the transformed signal to generate a modified transformed signal.

Identification of stationary signal components (e.g., peaks) and transient components may require additional manipulation of the transformed signals, the original time-based signal and/or a modified time-based signal. In one arrangement, a second transform is performed on the original time-based signal for a time window that includes the series of time periods in order to generate a transformed base signal. Preferably, this transformed base signal includes frequency and time components. Identification of stationary signal components and transient components may then be performed by comparing information from each of the series of transformed signals to a corresponding time and/or frequency component of the transformed base signal. In cases where there is good correlation between these signals, information may be identified as being stationary. In contrast when there is a substantial difference between the transformed base signal and a transformed signal for a given time period, the difference may indicate the existence of a transient event and hence artifact. Accordingly, such artifact may be removed from the transformed signal and/or the time-based signal to generate a modified transformed signal and/or a modified time-based signal.

According to a second aspect of the present invention, a utility if provided where an energy map is generated for a time window of a time-based signal corresponding to one or more optical signals received incident on the detector of a pulse oximeter. The energy map includes time duration and magnitude information for the time-based signal within the time window. Non-stationary or transient objects within the energy map are identified and removed in order to generate a modified energy map. Using the modified energy map, physiological patient data is generated. In one arrangement, a modified time-based signal is generated form the modified energy map that is substantially free of energy associated with one or more non-stationary objects within the time window. The modified time-based signal may then be utilized for, for example, blood analyte calculations.

Generation of the energy map typically requires that the time-based signal be transformed. For instance, one or more wavelet transforms may be performed on the time-based signal to generate a signal having both time and frequency information. As may be appreciated, frequency information may include duration information which is analogous to an inverse of frequency. In any case, the generated energy map may include time on a first axis and frequency information (e.g., duration) on a second axis as well as a representation of magnitude in a third dimension. In such a three dimensional model, values corresponding with areas of high energy in the time-based signal may be identified as peaks. Such peaks are often associated with artifact. Accordingly, the relative location of such peaks to other peaks within the signal may be analyzed to determine whether or not the high energy peak is repetitive. In this regard, repeating peaks may be identified as stationary objects that correspond to a desired signal component whereas non-repeating peaks may be identified as outliers/artifact corresponding to transient events. Accordingly, by identifying the time and frequency of a non-stationary peak (s), the peak may be removed (e.g., subtracted) from the energy map. As may be appreciated, this may remove a portion of a desired signal component. However, substantially all of the energy associated with the non-stationary peak may be removed while only a portion of a desired signal component may be removed resulting in an improved overall signal. In this regard, improved signal filtering may be achieved.

According to another aspect of the present invention, a utility is provided where a time-based signal is transformed over a first window to generate a first transform signal having at least a frequency component. This time-based signal is then transformed over a second time window to generate a second transform signal having at least a frequency component. The second time window is disposed within the first time window. In this regard, at least a portion of the same time-based signal is transformed for two different but at least partially overlapping time windows. At least a portion of the first and second transform signals are then compared (e.g., at a common time) to identify noise components in the first window. The noise components may then be subtracted from the first transform window to generate a modified transformed signal for the first time window. This modified transformed signal may then be utilized to generate physiological patient data. For example, an inverse transform may be performed on the modified transform signal to generate a modified time-based signal that is substantially free of the noise component. This modified time-based signal may then be processed in any appropriate manner.

According to another aspect of the present invention, a utility is provided where a wavelet transform is performed on a time-based signal that is reflective of one or more optical signals incident on a detector of a pulse oximeter. The wavelet transform generates a transformed signal having time, frequency and magnitude components. At least a first object is removed from the transformed signal based on at least a first criterion to generate a modified transformed signal. This modified transformed signal is utilized for pleth calculations.

The first object may be removed from the transformed signal in any appropriate manner. For instance, in cases where the wavelet transform is illustrated/plotted as an energy map, portions of that energy map may be graphically removed prior to, for example, inverse transforming the map to produce a modified time-based signal. Accordingly, information associated with the removed portions of the map are not inverse transformed. Alternatively, a frequency band may be masked prior to such an inverse transform. Accordingly, information outside of this band would be excluded from such an inverse transform and a resulting output signal. In a further alternative, peaks may be identified within the transform signal and then, a transient nature of those peaks may be determined to identify artifact.

According to another aspect of the present invention, a utility is provided where a dual wavelet transform is performed on a time-based pleth signal in order to identify and remove nonstationary events from the time-based signal. In this regard, the first wavelet transform is performed on a first portion of the time-based signal. This first wavelet transform has a narrow time window and a wide frequency band to allow for identifying peaks within the time-based signal. A second wavelet transform may then be performed on a second portion of the time-based signal. This second wavelet transform may have a wide time window and a narrow frequency band in order to better identify repeating events within the time window. By comparing the results of the first and second wavelet transforms, objects within the time-based signal may be identified as repeating or transient. In this regard, transient events may be removed from the signal. Accordingly, a time-based signal substantially free of transient events may be generated.

DETAILED DESCRIPTION

The present invention relates generally to obtaining physiological parameter information for a patient based on an analysis of a pleth signal. More specifically, the present invention is related to distinguishing effects associated with artifact from a signal portion of interest in a raw pleth signal such that the effects associated with motion may be attenuated or removed prior to use of the pleth for obtaining physiological parameter information. In the following discussion, the invention is described in the context of an implementation utilizing components of a conventional two-channel pulse oximeter. However, it will be appreciated that various aspects of the invention are not limited to such a pulse oximeter or other multi-channel signal implementation and the invention may be embodied in a dedicated single or multi-channel photoplethysmography instrument. Accordingly, the following discussion should be understood as exemplifying the invention and not by way of limitation.

Figure 1:
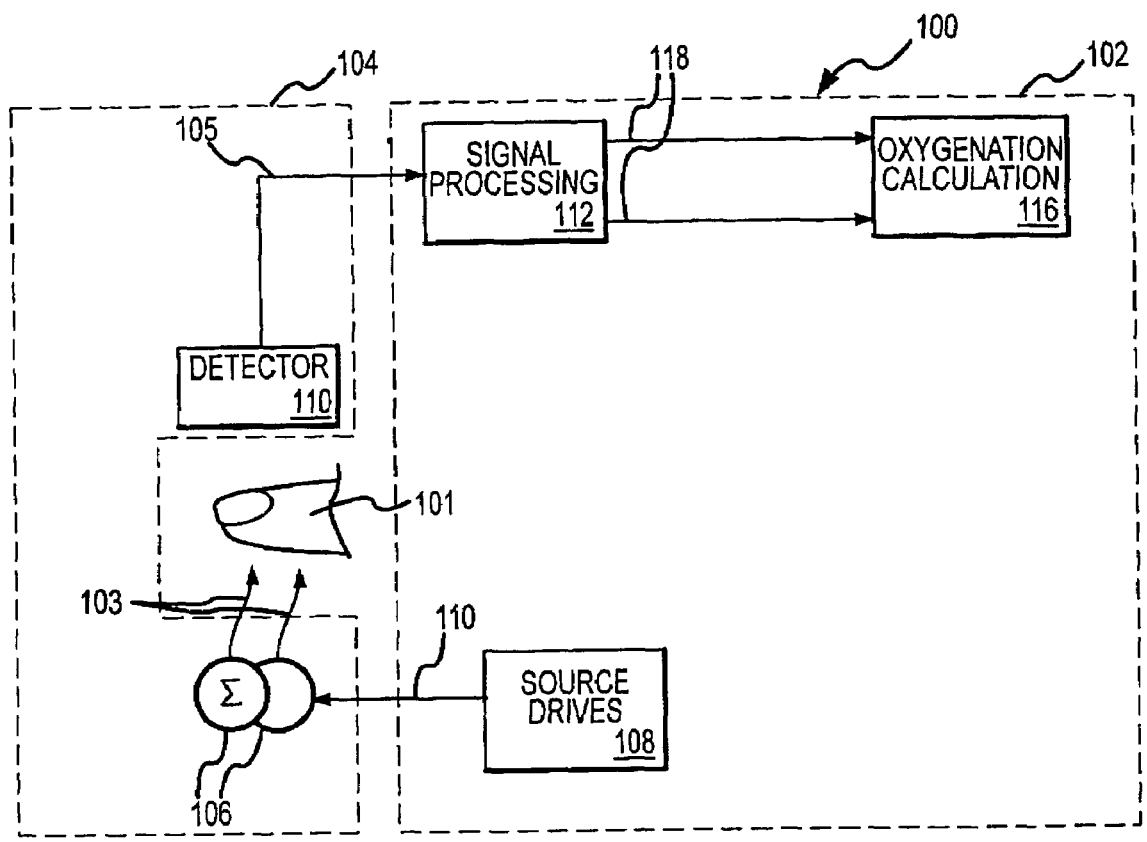
FIG. 1 illustrates an exemplary pulse oximetry systems.

Referring to FIG. 1, a schematic diagram of a pulse oximeter 100 in accordance with the present invention is shown. The oximeter 100 generally includes an instrument housing 102 and a probe 104 for attachment to a finger 101 or other appendage of a patient under analysis. In the illustrated embodiment, the probe 104 includes two or more sources 106 and a detector 110. It will be appreciated that either or both of these components may alternatively be located in the housing 102 and may be optically connected to the probe 104 by fiber optics or the like. Additionally, the sources 106 and/or detector 110 may be located in the cable or other coupling operatively between the probe 104 and the housing 102. The sources 106 are driven by source drives 108. The drives 108 serve to modulate the signals 103 in any of various ways. In this regard, the signals 103 transmitted by the sources 106 may be time division multiplexed, frequency division multiplexed, code division multiplexed, or the like. Such multiplexing facilitates separation of the signals from each of the channels during hardware or software based signal processing. The sources 106 provide two or more channels of signals 103. Each channel has a unique spectral content, e.g., wavelength or wavelength band. In the illustrated embodiment, two sources 106 are shown; one of the sources may have a red-centered wavelength and the other may have an infrared-centered wavelength.

The signals 103 may be transmitted through or reflected by the patient's tissue. In either case, the signals are modulated by the patient's tissue to provide information regarding blood oxygen saturation in a manner that is well known. The transmitted signals 103 are received by the detector 110 which, in the illustrated embodiment, provides an analog current output signal 105 representative of the detected signals 103. This detector signal 105 is then processed by signal processing module 112. The processing module 112 may include a number of components that may be embodied in software, firmware and/or hardware. These components may include components for amplifying the signal 105 and converting the signal from a current signal to a voltage signal. Further, the processing module may filter the signal to remove certain components of noise and otherwise conditioning the signal, as will be more fully discussed herein.

In the illustrated embodiment, the signal processing module 112 also includes an analog to digital converter for converting the signal into a digital signal and a demultiplexer component for providing two separate output signals 118 or pleths that generally correspond to the two separate channel signals 103. These pleths 118 are then used by oxygenation calculation module 116 to compute a value related to blood oxygen saturation, e.g., a blood oxygen saturation percentage. A number of algorithms for performing such calculations are known and such calculation techniques are disclosed in U.S. Pat. No. 5,934,277 by Mortz and U.S. Pat. No. 5,842,979 by Jarman, both of which are incorporated herein by reference.

Figure 2:
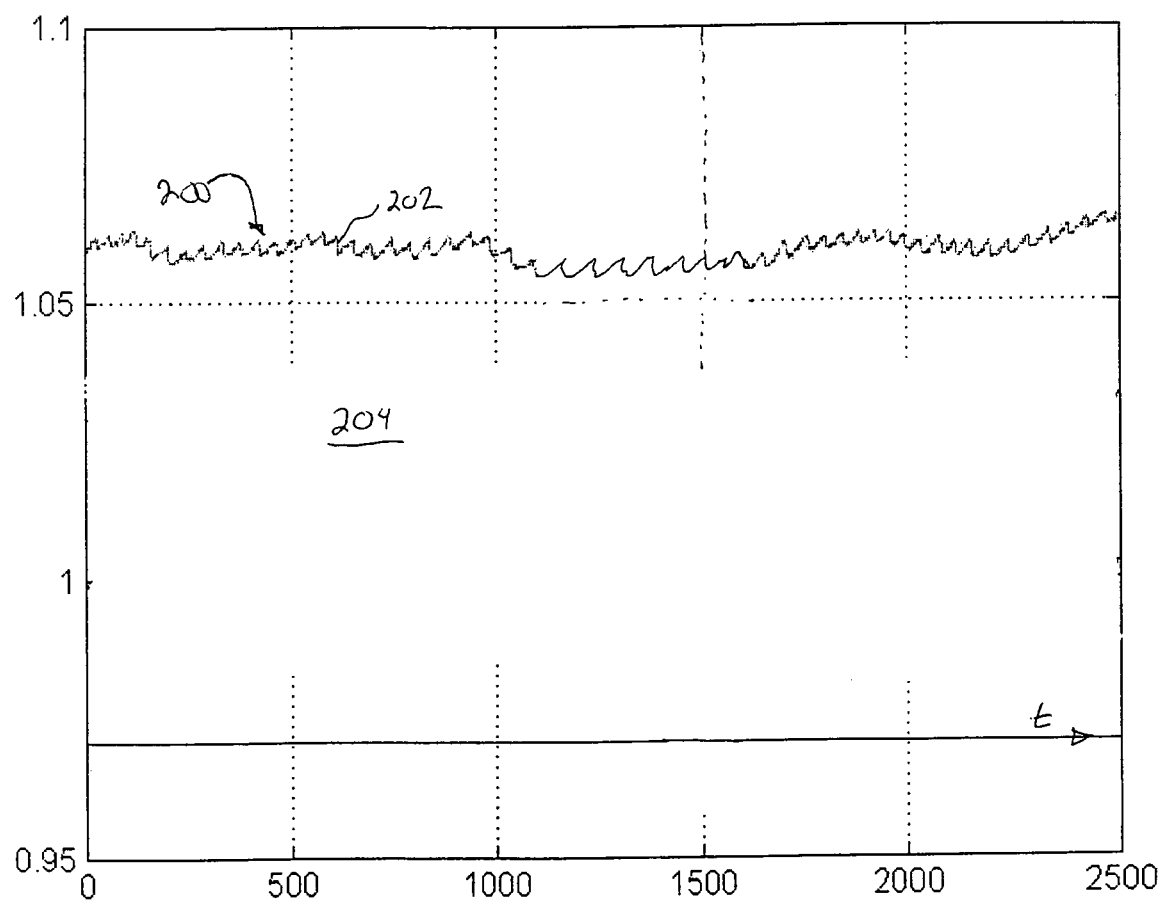
FIG. 2 illustrates a substantially clean pleth signal.

FIG. 2 generally illustrates an exemplary raw pleth waveform corresponding to one of the optical channels (e.g., red or IR). As used herein, the term "raw" is utilized to denote a pleth signal that has not been filtered or otherwise processed. As shown, the waveform 200 generally includes a pulsatile or AC signal component 202 having a relatively small magnitude carried by a baseline or DC signal component 204 of larger magnitude. When the AC signal component 202 can be isolated from the raw pleth signal 200, this component 202 is typically utilized to determine physiological parameters (e.g., blood oxygenation) in pulse oximetry applications. In instances where the AC component 202 cannot be isolated from the raw pleth signal due to the presence of motion or other artifact, the DC component 204 may be utilized to determine physiological parameters. Use of the baseline DC component for pulse oximetry calculations is sometimes referred to as DC tracking.

The use of the baseline DC component 204 at times when the pulsatile or AC component 202 cannot be determined may, in some instances, provide adequate data for use in determining physiological parameters. However, the DC signal component 204 tends to drift over time due to one or more physiological conditions including, without limitation, respiration, respiratory sinus arrhythmia and the Meyer wave. The drift of the DC signal component 204 may, over time, result in inaccurate calculation of physiological parameters. Accordingly, it is preferable to utilize the AC signal component 202 when available. Typically, the AC signal component 202 can be identified from a pleth waveform 200 when little or no artifact is present. For instance, FIG. 2 shows a clean pleth waveform 200 that is substantially free of artifact/noise and it would be expected that the AC signal component 202 could readily be identified. However, in most applications some artifact is present at least during a portion of the monitoring process such that the resulting pleth waveform includes one or more periods of artifact/motion.

Figure 8:
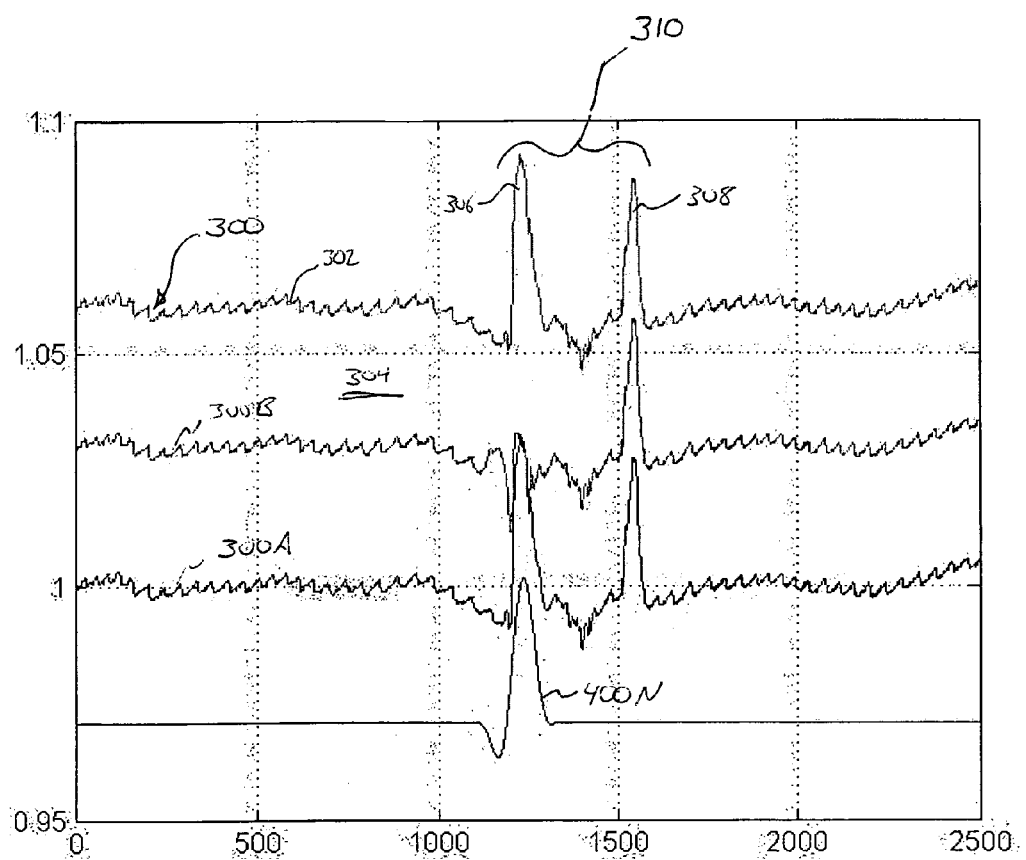
FIG. 8 illustrates a pleth containing an artifact period.

Referring briefly to FIG. 8, a pleth waveform 300 is illustrated that includes an artifact period 310 during which determination/isolation of the AC signal component 302 may be difficult. As shown, the artifact period 310 is generally defined between first and second artifact spikes 306 and 308. This artifact period 310 corresponds to motion or other noise present during pleth data acquisition and tends to overwhelm the AC signal component 302 of the pleth signal 300. Accordingly, during prolonged artifact periods 310, the accepted practice has been to utilize DC tracking for plethysmographic calculations due to the inability to effectively filter/isolate the AC signal component 302 from the artifact. However, it has been recognized that while the magnitude of the artifact in the artifact period 310 overwhelms the AC signal component 302 of the pleth signal 300 the AC signal component 302 may still be present within the artifact period 310 of the pleth signal. In effect the high energy of the artifact masks the AC signal component 302 of the pleth signal 300. Accordingly by removing energy primarily associated with individual artifact events (e.g., artifact spikes 306, 308) from the pleth signal 300, the underlying AC component may be 'unmasked' and utilized for subsequent plethysmographic calculation. In this regard, DC tracking may be avoided. Stated otherwise, by removing the motion artifact/noise from the pleth signal 300 it may be possible to identify all or at least a portion of the AC signal component 302 for use in subsequent calculations.

In order to separate the energy associated with the artifact from energy associated with the AC signal component 302, it is necessary to analyze both the time and frequency components of the pleth signal. Various options exist for performing such a dual-component analysis of the pleth signal 300 where time and frequency components are analyzed to identify individual signal characteristics. For instance, a series of Fourier transforms may be performed for successive short time periods of the pleth signal. The resulting signal provides a series of frequency spectrums indexed versus time. However, as set forth herein, a wavelet transformation(s) is utilized to generate frequency and time information for analyzing the pleth signal 300.

Figure 3A:
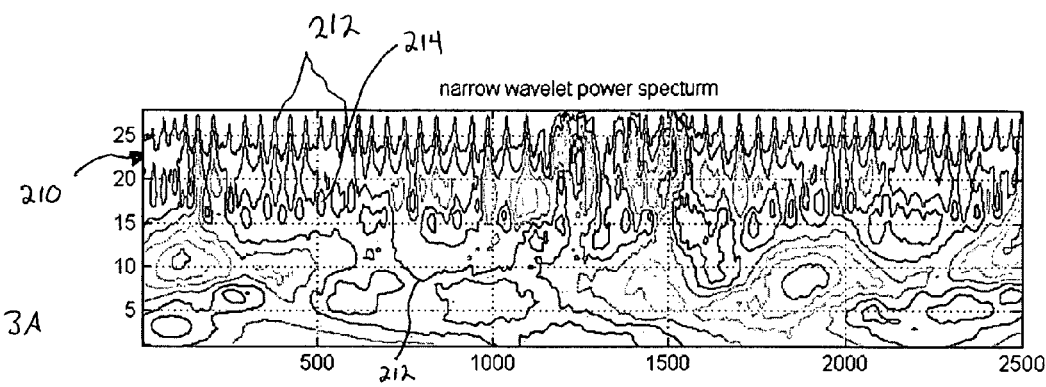
FIGS. 3A-3C illustrate transformations of the signal of FIG. 2.

FIG. 3A illustrates a plot of an exemplary wavelet transformation (e.g., a time and frequency analysis) of the substantially clean pleth waveform 200 of FIG. 2. The use of a wavelet to transform the pleth signal 200 will be more fully discussed herein. As shown, the horizontal axis is a time axis that corresponds with a number of data samples (e.g., 2500 samples) of the pleth signal in the time domain while the vertical axis represents a frequency axis. More specifically, the vertical axis is analogous to an inverse frequency or 'duration'. The lines 212 within the plot represent the magnitude of the transformed pleth signal 200 in both time and frequency. Stated otherwise, the wavelet transform of the pleth signal 200 is an energy map or power spectrum 210 that is analogous to a topology map. In this regard, the 'contour' lines 212 represent a magnitude of the signal at corresponding time and frequency locations. Of note, a peak 214 within the power spectrum 210 represents an area of high energy that may correspond to a desired signal component (e.g., AC component) or an undesired signal component/artifact.

Figure 4:
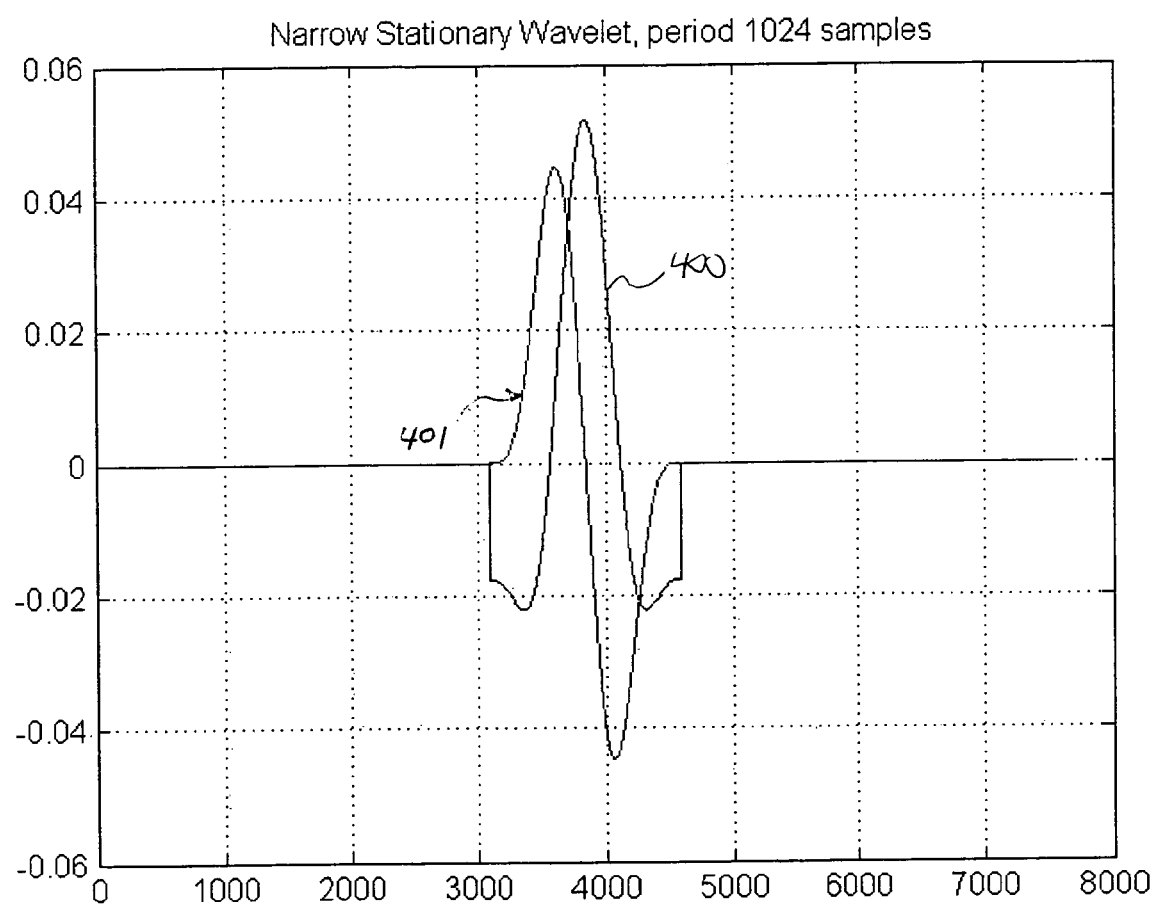
FIG. 4 illustrates a first wavelet.
Figure 5:
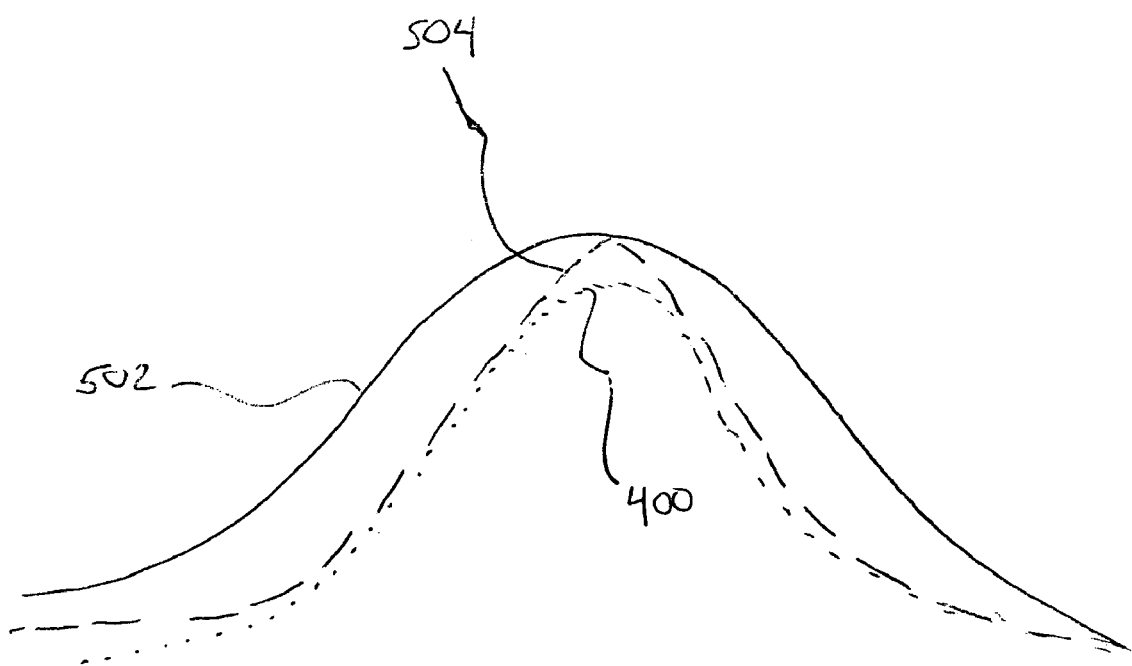
FIG. 5 illustrates application of the wavelet of FIG. 4 to a waveform.

As shown in FIG. 2 and 3A, the series peaks associated with the AC signal component 302 are represented as a series of repeating objects by the contour lines 212 in the power spectrum 302. Specifically, the series of peaks are represented by the series of repeating objects between about 20 and 30 on the vertical frequency axis and extending across the time axis. Of note, the exact configuration of a particular energy map/power spectrum is dependent on the type of wavelet selected for transforming a given signal. That is different wavelets will generate different energy maps/power spectrums. In this regard, various types of wavelets may be utilized and their selection is a matter of design choice. For instance, Harr wavelets, Morlet wavelets, Mexican hat wavelets as well as raised cosine wavelets represent a short non-inclusive list of potential wavelets that may be utilized to transform a pleth signal for frequency and time-based analysis FIG. 4 illustrates a wavelet that may be utilized to generate the energy map/power spectrum of FIG. 3A. As shown, the wavelet of FIG. 4 is a narrow wavelet 400 having a time period that is small in comparison with its frequency band. The shape of the narrow wavelet 400 is selected to allow for matching with individual peaks in the time-based pleth waveform signal 200. As shown in FIG. 5, a Blackman window on top of a sine wave 502 is utilized to identify peaks within the pleth signal 200 such that one or more narrow wavelets 400 may be fit to an identified peak 504. In this regard, the narrow wavelet(s) 400 may be expanded or contracted along the time axis and/or amplitude axis to allow shape matching with the identified peak. Further, different portions of multiple narrow wavelets 400 may be applied to a single identified peak to match the identified peak. A series of narrow wavelets 400 are applied to replicate the features of the pleth signal 200 over a time window. However, it will be appreciated that each wavelet 400 includes information relating to the entire time window of the pleth signal 200 as shown in FIG. 2. This results in the generation of the additional signal information that requires mapping the transformed signal as a function of both time and duration as a narrow wavelet energy map/power spectrum 210. In summary, the use of the narrow wavelet 400 allows for one or more wavelets to be matched to individual peaks in a time-based signal to replicate (i.e., transform) the time-based signal. Note that a quadrature sine based wavelet 401 is also shown in FIG. 4. Using both the cosine based wavelet 400 and the quadrature (sine based) counterpart 401 permits more accurate modeling of artifact. See 400N on FIG. 8, which is a combination of 400 and 401.

Figure 3B:
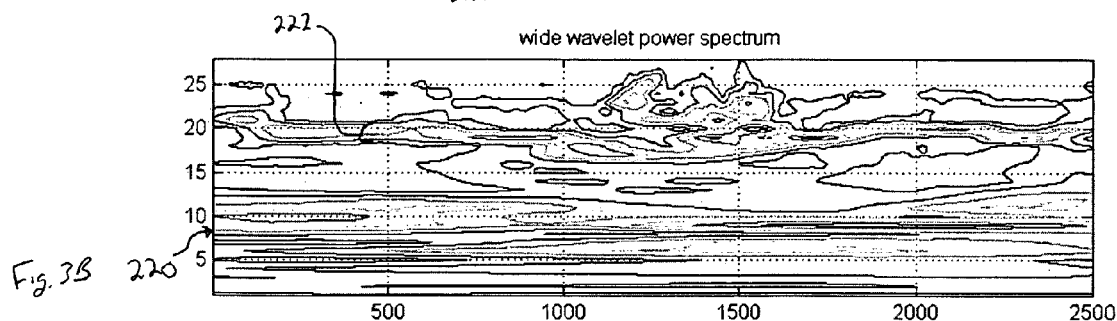
Figure 6:
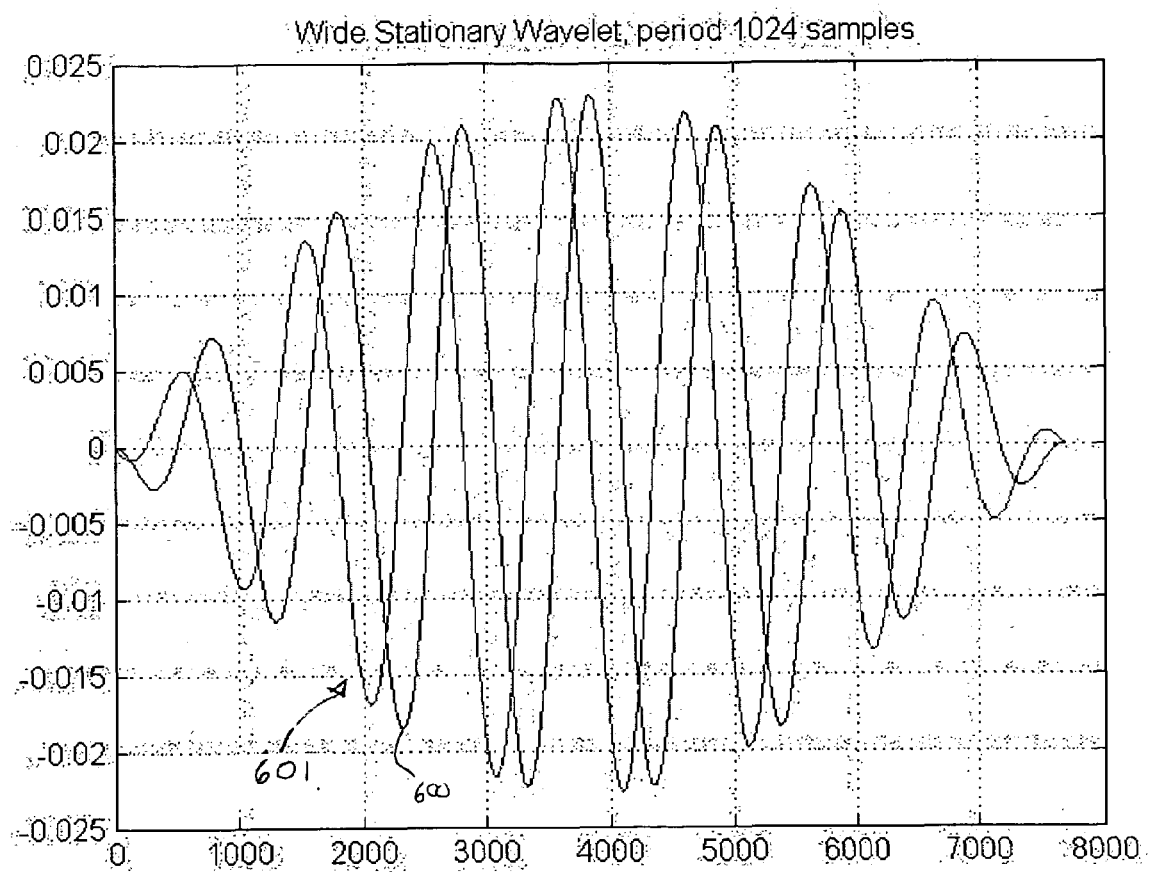
FIG. 6 illustrate a second wavelet.
Figure 7:
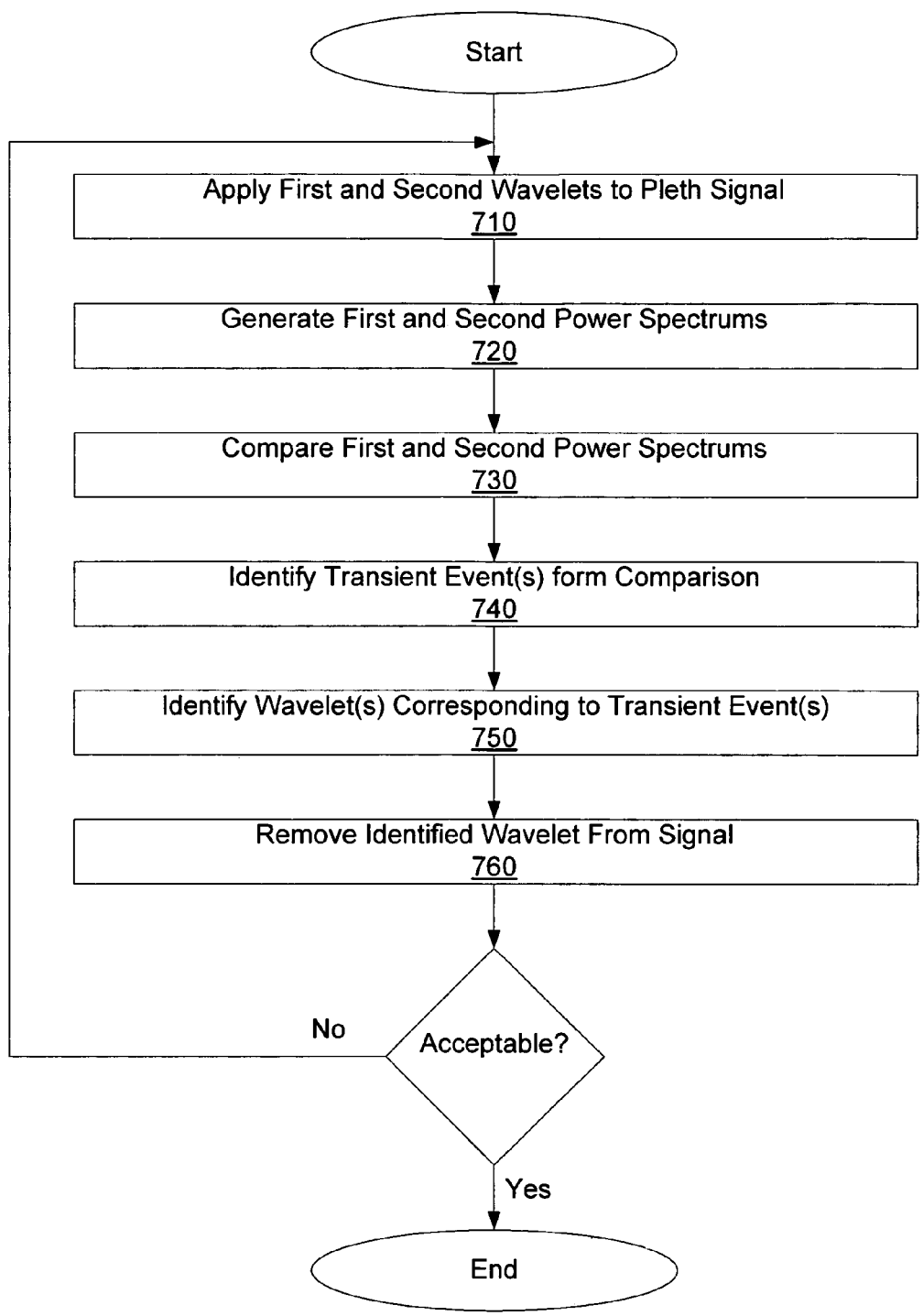
FIG. 7 illustrates a process flow sheet.

FIG. 6 illustrates a second wide wavelet 600 and it quadrature counterpart 601. In contrast to the first narrow wavelet 400, the second wide wavelet 600 has a wide time window compared to its frequency band. In this regard, when the second wide wavelet 600 is applied to the pleth waveform 200, the wide wavelet 600 encompasses several pulsatile peaks of the pleth signal 200 (not shown). Transforming using both the cosine base wavelet 600 and its quadrature counterpart 601 permits motoring the power at the time-frequency point while reducing the impact or entirely ignoring phase information. This results in a wide wavelet power spectrum as shown in FIG. 3B. In this regard, the wide wavelet 600 is not utilized to identify individual peaks within the pleth waveform 200, but rather, the wide wavelet 600 is useful to identify repeating events within the pleth waveform 200. For instance, in the wide wavelet power spectrum 220 of FIG. 3B a stationary band 222 between about 17 and 22 on the vertical frequency axis and extending across the time axis corresponds to the repeating pulsatile AC component of the pleth signal 220. Stated otherwise, repeating events such as an AC signal component are represented as stationary areas or 'stationalities' within the wide wavelet power spectrum plot 220. A clearer view of a stationary band 222 corresponding to the AC signal component is shown on FIG. 13B.

Figure 3C:
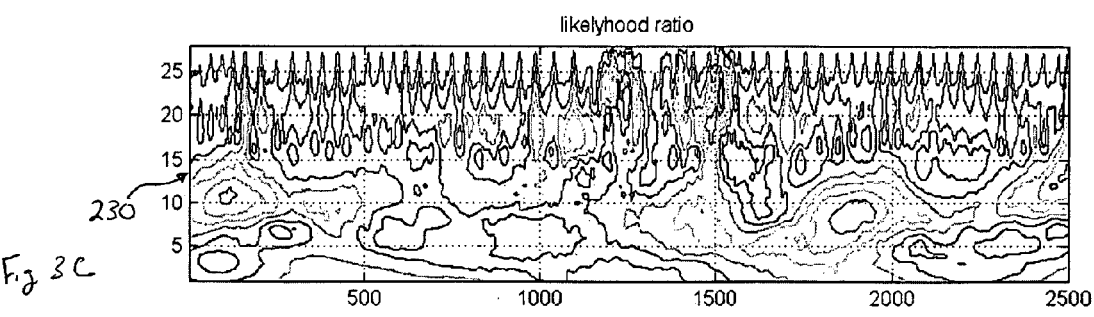

Referring again to FIGS. 3A-3C, the first and second power spectrums 210, 220 may be compared to identify differences between the spectrums that may be indicative of outlying data points such as artifact. In this regard, the first power spectrum 210 may be divided by the second power spectrum 220. This comparison results in a difference ratio map 230 as illustrated in FIG. 3C. As noted, the narrow wavelet 400 identifies peaks and the wide wavelet 600 identifies stationary areas related to repeating objects. If these wavelets 400, 600 were applied to a substantially constant repeating pleth signal such as pleth signal 200 having no appreciable motion artifact peaks, the ratio of the power spectrums 200 and 210 would be substantially equal over the time window and frequency window as shown in FIG. 3C. That is, there would be no areas on the ratio map that have a significantly larger amplitude than other areas; there would be no areas of poor correlation. If one or more areas of poor correlation exist, each such area may be indicative of an artifact/transient event. Further the time, and frequency of the artifact event may be determined from the ratio map. The magnitude of the artifact event may be determined by identifying the narrow wavelet associated with that time. Accordingly, the energy associated with that artifact event may be removed from the pleth signal as will be discussed herein.

As set forth in FIGS. 7-9C, a process (700) is described where a pleth signal including an artifact period 310 is cleaned using a time and frequency analysis. As shown, FIG. 8 illustrates four waveforms including the original pleth 300, a current pleth 300A, a narrow wavelet 400N corresponding to one artifact spike (306 as illustrated), and a resulting or modified pleth 300B. As will be discussed herein, the narrow wavelet 400N is subtracted from the current pleth 300A to generate the modified pleth 300B. Of note, in FIG. 8 prior to the removal of a first artifact event from the original pleth 300, the original pleth 300 and the current pleth 300A are identical.

Figure 9A:
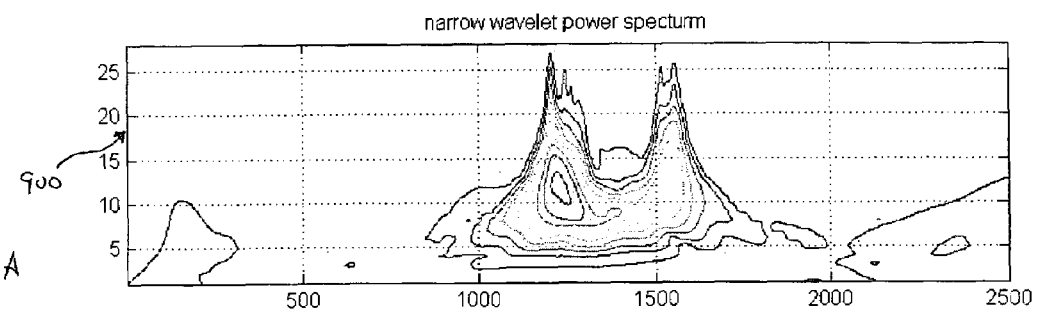
FIGS. 9A-9C illustrate transformations of the signal of FIG. 8.
Figure 9B:
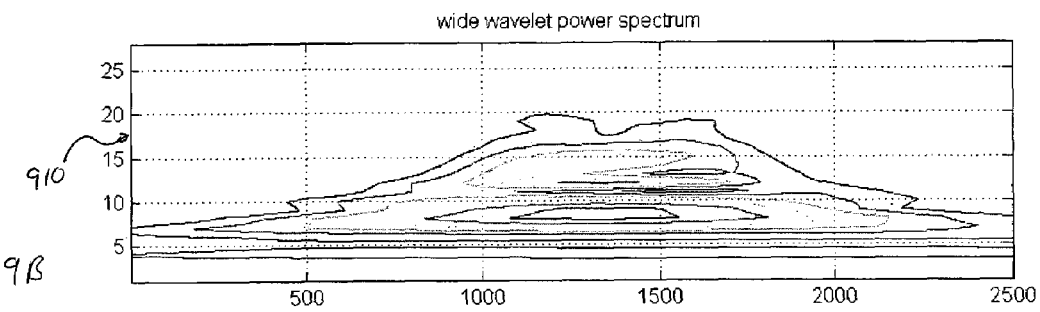

To begin the process (700) of removing artifact events from the pleth 300, the first and second wavelets 600, 800 are applied (710) to the original pleth 300 to generate (720) first and second energy maps/power spectrums. These power spectrums are shown in FIGS. 9A and 9B. Specifically, FIG. 9A illustrates the application (710) of the narrow wavelet 400 to the original pleth 300. As shown, the energy associated with the two large artifact spikes 306, 308 in the original pleth 300 represent areas of high energy in the narrow wavelet power spectrum 900, points 906 and 908. This is expected as the narrow wavelet 600 is by design meant to effectively replicate peak events in a time-based signal.

The result of the application (710) of the wide wavelet 600 to the pleth waveform 300 is illustrated in FIG. 9B. As with the narrow wavelet spectrum 400, the wide power spectrum 410 shows an area where the energy of the two large artifact spikes 306, 308 is present. However, as the wide wavelet power spectrum is directed to identifying repeating events (i.e., stationalities) the generally random artifact spikes 306, 308 are not represented in the wide power spectrum 910 to the extent of their representation in the narrow power spectrum 900.

Figure 9C:
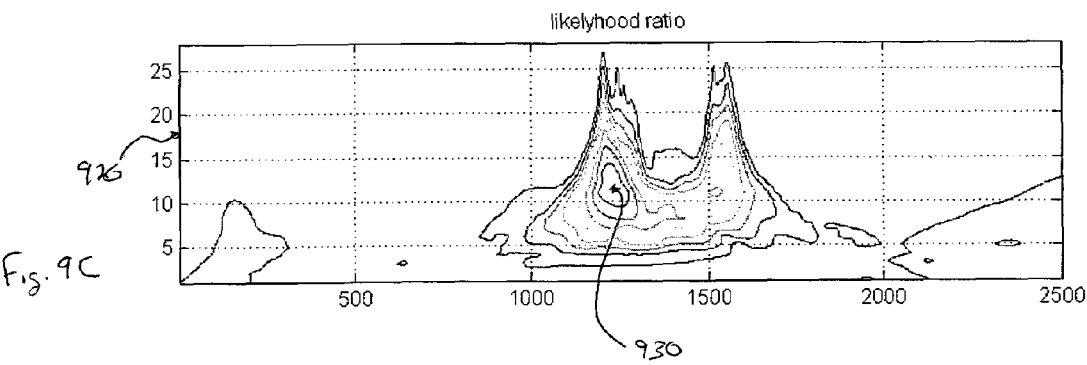

The first and second power spectrums 900 and 910 are then compared (730) in order to identify differences therebetween. In this regard, the first power spectrum 900 may be divided by the second power spectrum 910. This comparison (730) results in a difference ratio map 920 as illustrated in FIG. 9C. As shown, the artifact spikes within the pleth signal 300 result in areas of non-correlation (e.g., non-stationary/transient events) in the difference ratio map 920. In this regard, by identifying (740) at least one transient peak 930 (e.g., the largest peak) within the difference ratio map 920 a time, frequency, and magnitude component can be identified (750) for removal (760) from the original pleth waveform 300.

More specifically, the second identification step (750) may entail selecting the narrow wavelet 400N associated with the time of the non-stationary peak 930 identified (740) from the ratio map. This particular wavelet 400N is shown in FIG. 8. The identified narrow wavelet 400N is subtracted (760) from the current pleth 300A to generate a modified pleth 300B. The modified pleth 300B is best shown in FIG. 10, where it becomes the current pleth 300A when/if the process (700) is repeated.

After the narrow wavelet is subtracted (760) from the current pleth 300A, a determination (770) is made as to whether the current pleth 300A is within a predetermined acceptable range or if it is desirable/necessary to remove additional artifact from the current pleth. If the current pleth 300A is acceptable, the process (700) ends and the current pleth 300A may be utilized for subsequent pulse oximetry calculations. If it is necessary to remove additional artifact to produce an acceptable pleth, the process (700) is repeated. In this embodiment, the process (700) is an iterative process.

Figure 10:
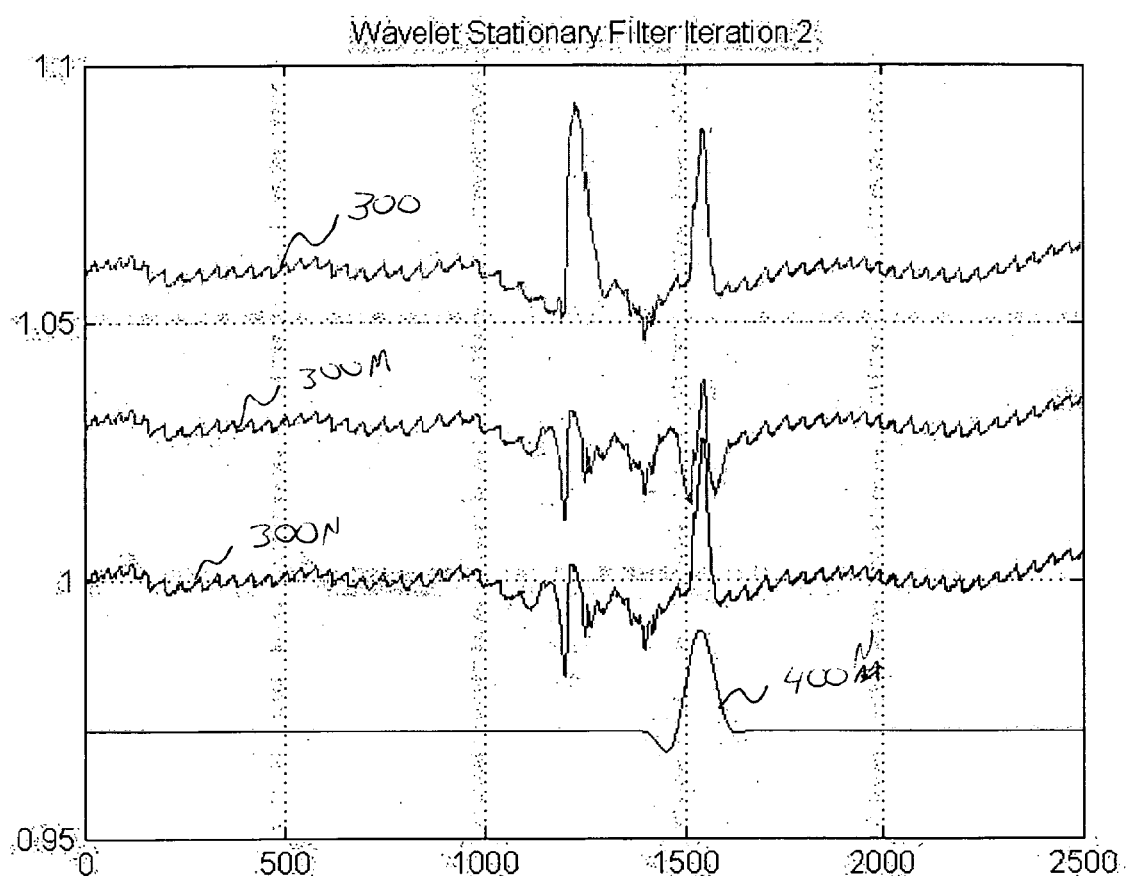
FIGS. 10-14 illustrates modified pleth waveforms and corresponding power spectrums.
Figure 11A:
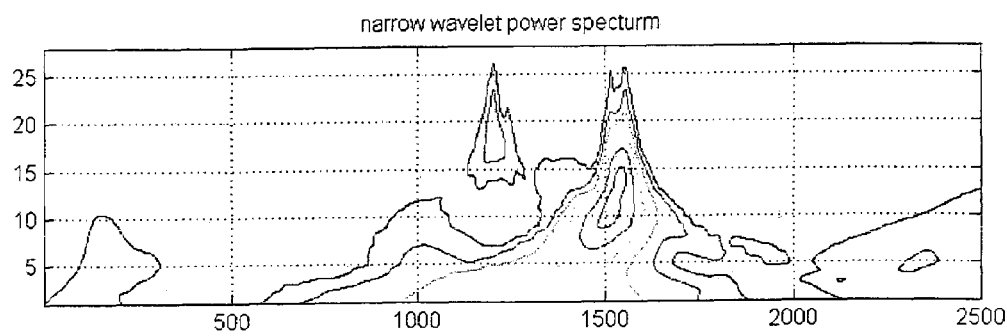
Figure 11B:
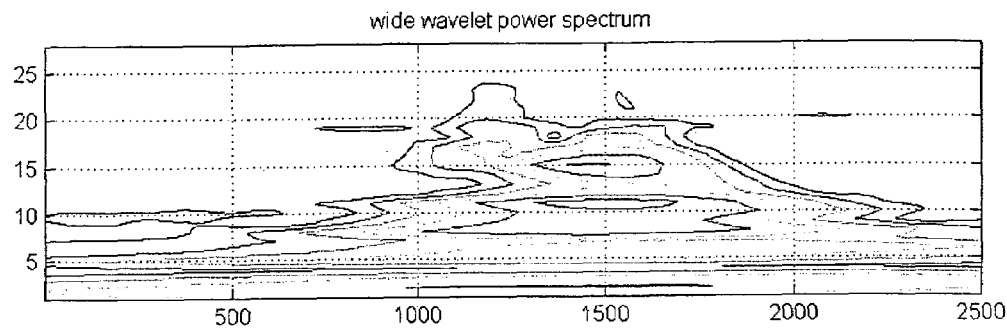
Figure 11C:
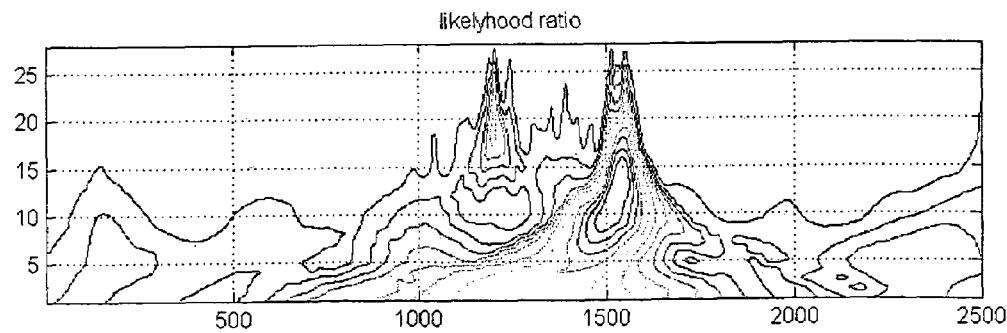
Figure 12:
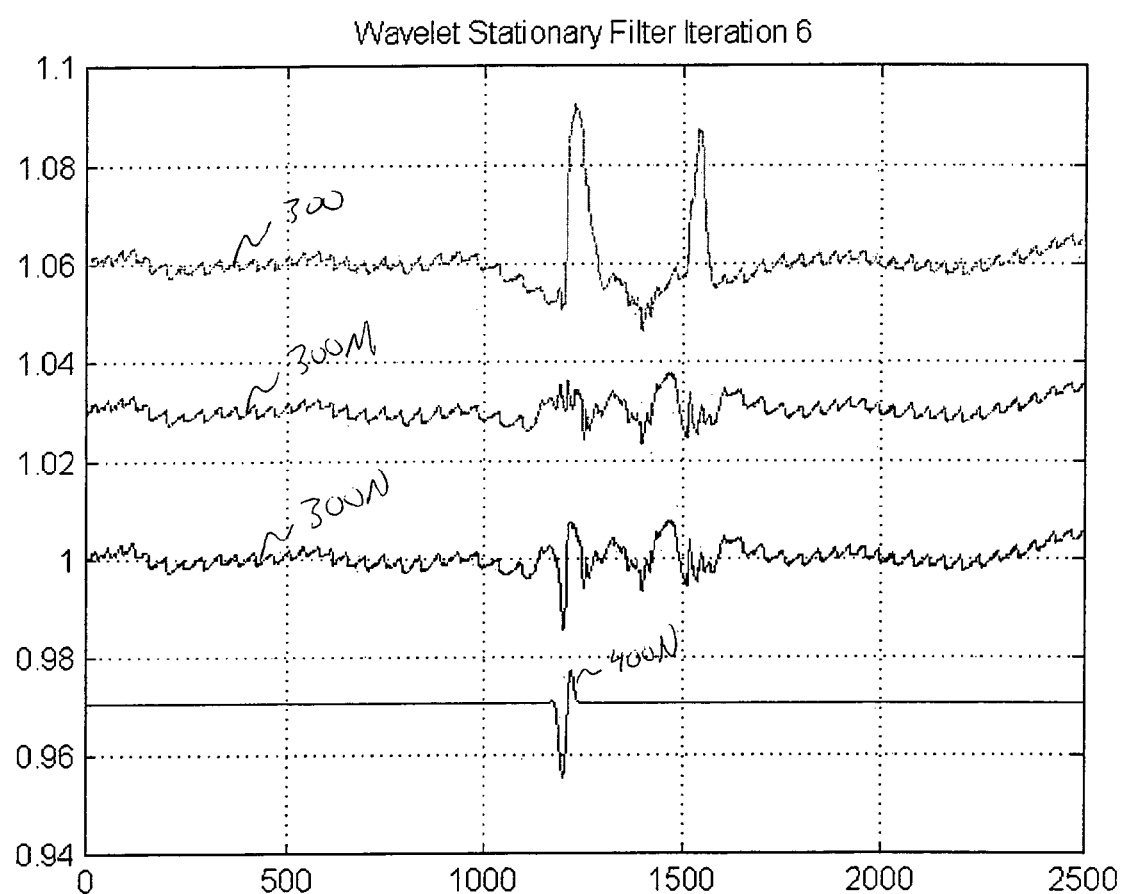
Figure 13A:
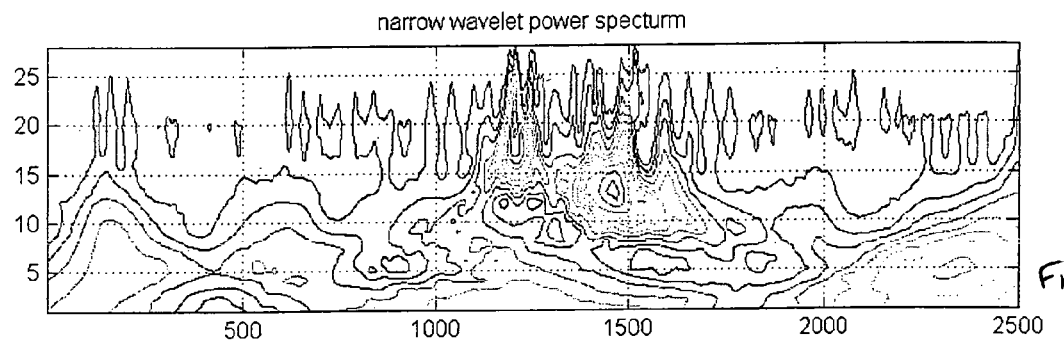
Figure 13B:
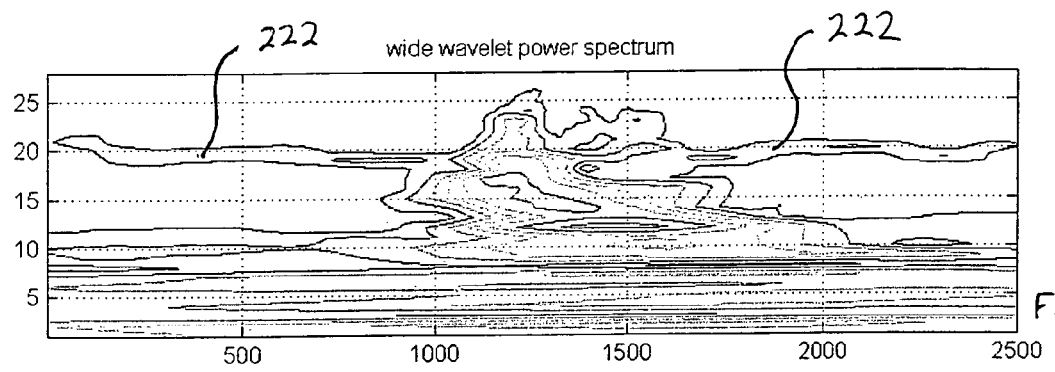
Figure 13C:
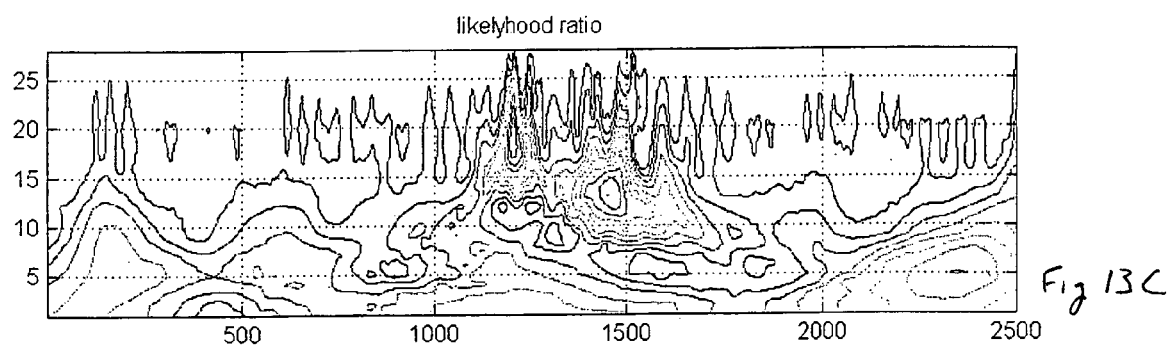
Figure 14:
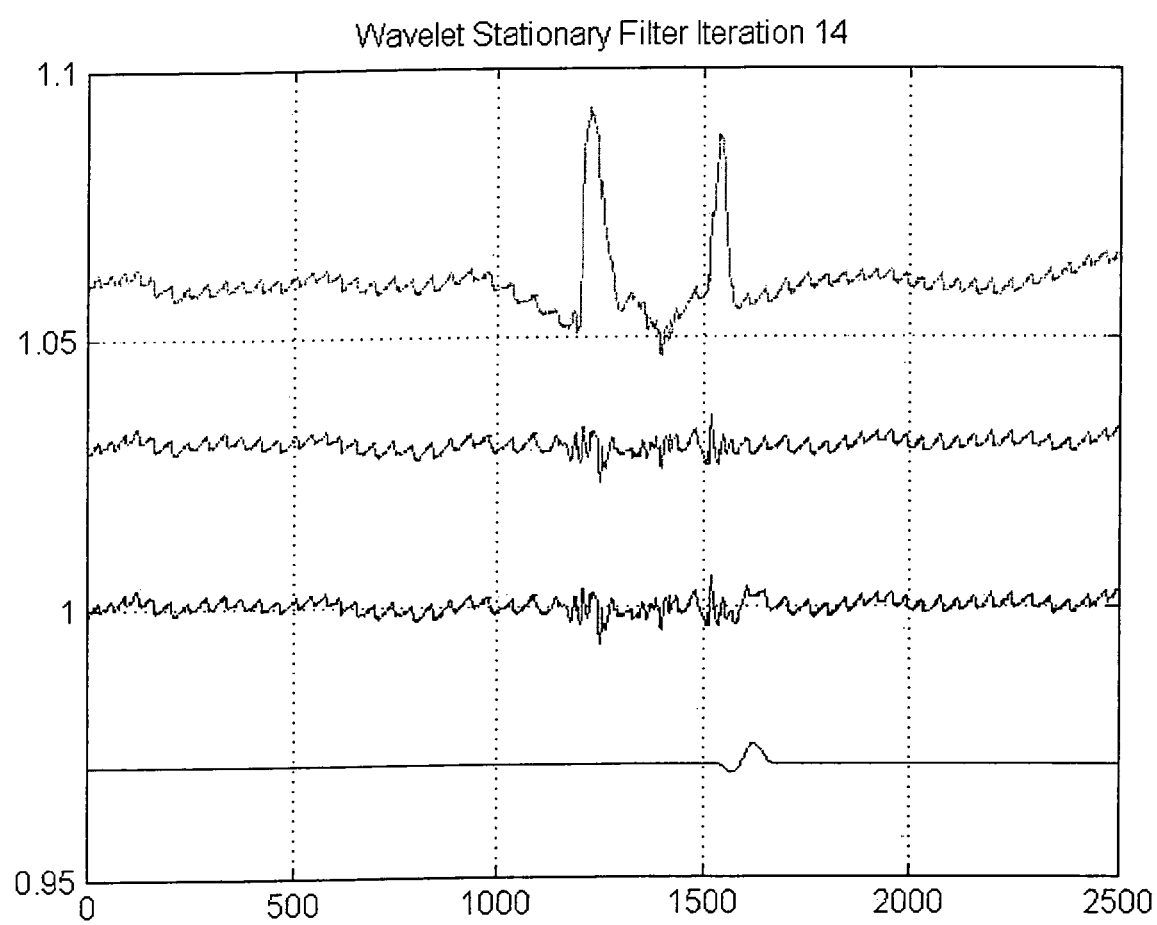

FIGS. 10-14 illustrate further iterations where additional differences between the narrow and wide power spectrums are identified and removed from the current pleth 300N. Specifically FIGS. 10 and 11 illustrate waveforms and spectrums for a second iteration, respectively; FIG. 12 and 13 illustrate waveforms and spectrums for a sixth iteration, respectively; and FIG. 14 illustrate waveforms for a fourteenth iteration. In each subsequent iteration, the application of the wavelets 400, 600 is performed to generate additional power spectrums and difference ratios. Likewise, non-stationary peaks are identified such that a corresponding narrow wavelet 400N may be removed form the current pleth 300N to generate a modified pleth 300M.

Referring to FIGS. 12 and 14, it will be noted that as the energy of artifact events are removed from the current waveform 300N, peaks associated with the AC signal component 302 of the original pleth waveform 300 begin to appear in the power spectrums. That is, the removal of the artifact energy allows for unmasking desired portions of the original signal 300N.

Though discussed above as an iterative process, it will be appreciated that multiple non-stationary peaks may be identified and removed from the waveform 300 in a single step. Furthermore, it will be appreciated that rather than removing the narrow wavelets 400N from the current pleth waveform 300N, the narrow wavelets may be removed from the narrow wavelet power spectrum. The narrow wavelet power may subsequently be inverse transformed to generate a time-based pleth signal. In conjunction with removal of a particular wavelet, one or more areas of the narrow wavelet power spectrum may be masked (e.g., frequency bands) prior to performing an inverse transform. Of further note, identical processes may be performed on the red and IR channels of the pulse oximeter such that each signal is cleansed.

The foregoing description of the packaging design has been presented for purposes of illustration and description. Furthermore, the description is not intended to limit the invention to the form disclosed herein. Consequently, variations and modifications commensurate with the above teachings, and skill and knowledge of the relevant art, are within the scope of the invention. The embodiments described hereinabove are further intended to explain best modes known of practicing the invention and to enable others skilled in the art to utilize the invention in such, or other embodiments and with various modifications required by the particular application(s) or use(s) of the invention. It is intended that the appended claims be construed to include alternative embodiments to the extent permitted by the prior art.

What is claimed:

1. A method for processing a signal in a pulse oximetry device, comprising the steps of:
   receiving, at an inlet port of a pulse oximetry device, a time-based signal reflective of one or more optical signals incident on a detector of a pulse oximeter sensor, said time-based signal being attenuated by patient tissue;
   using a processor of said pulse oximetry device;
      first transforming a series of time periods of said time-based signal to generate a first series of transformed signals each having at least a frequency component;
      second transforming at least a portion of said series of time periods of said time-based signal to generate a second series of transformed signals each having at least a frequency component;
      monitoring said first and second series of transformed signals to identify one or more frequency bands of one or more of said transformed signals that is potentially corrupted by artifact;
      upon identifying one or more of said frequency bands that is potentially corrupted by artifact for at least one of said first and second series of transformed signals, removing said one or more frequency bands from said at least one of said series of transformed signals to generate at least one modified transformed signal; and
      processing said at least one modified transformed signal to obtain physiological information regarding said patient tissue.

2. The method of claim 1, wherein processing comprises using said processor to perform an inverse transform on said at least one modified transformed signal to generate a modified time-based signal.

3. The method of claim 1, wherein obtaining comprises using said processor to process said at least one modified transformed signal to identify a blood analyte value.

4. The method of claim 1, wherein said transforming steps comprise generating transformed signals each having at least a frequency component and a time component.

5. The method of claim 4, wherein said first transforming step comprises performing a first wavelet transform, and said second transforming step comprises performing a second wavelet transform, wherein said first and second wavelet transforms are different.

6. The method of claim 1, wherein a first frequency band is removed from a first transformed signal of said first series of transformed signals and a second frequency band is removed from a second transformed signal of said first series of transformed signals, wherein said first and second frequency bands are different.

7. The method of claim 1, wherein said receiving step comprises:
   receiving first and second optical signals having different wavelengths; and
   separating said first and second optical signals into first and second time-based signals, wherein said transforming, monitoring, removing and processing steps are individually performed on said first and second time-based signals.

8. The method of claim 7, wherein said receiving step comprises receiving red and infrared optical signals.

9. The method of claim 1, wherein said first and second series of transformed signals includes at least a frequency component and a time component.

10. The method of claim 9, wherein said monitoring step further comprises:
    comparing each of said first series of transformed signals to a corresponding time and frequency component of said second series of transformed signals.

11. The method of claim 10, wherein said comparing step identifies objects within each of said series of transformed signals as at least one of:
    stationary objects in relation to at least one of said first and second series of transformed signals ; and
    transient objects in relation to at least one of said first and second series of transformed signals.

12. The method of claim 11, wherein said transient objects define said frequency band of each said transformed signal that is potentially corrupted by artifact.

13. The method of claim 1, wherein said series of time periods are successive.

14. The method of claim 1, wherein said series of time periods at least partially overlap.

15. A method for processing a signal in a pulse oximetry device, comprising the steps of:
    receiving, at an inlet port of a pulse oximetry device, a time-based signal reflective of one or more optical signals incident on a detector of a pulse oximeter sensor;
    using a processor of said pulse oximetry device:
       first generating a first energy map for a time window of said time-based signal, wherein said first energy map includes time, duration and magnitude information for said time-based signal within said time window;
       second generating a second energy map for at least a portion of said time window of said time-based signal wherein said second energy map includes time, duration and magnitude information for said time-based signal within said portion of said time window;
       based on a comparison of said first and second energy maps, identifying at least one transient object within one of said first and second energy maps;
       removing said at least one transient object from at least one of said first and second energy maps to generate a modified energy map; and
       using said modified energy map to generate physiological patient data.

16. The method of claim 15, further comprising:
    generating a modified time-based signal using said modified energy map.

17. The method of claim 16, further comprising:
    using said modified time-based signal to identify a blood analyte value.

18. The method of claim 16, wherein energy associated with said at least one transient object is substantially removed from said modified time-based signal.

19. The method of claim 15, wherein said first generating step comprises performing a first transform on at least a portion of said time window.

20. The method of claim 15, wherein said first generating step comprises performing a first wavelet transform on at least a portion of said time window.

21. The method of claim 20,
wherein said second generating step comprises performing a second wavelet transform on at least a portion of said time window.

22. The method of claim 21, wherein said first wavelet transform comprises a wavelet having a narrow time component relative to frequency and said second wavelet transform comprises a wavelet having a wide time component relative to frequency.

23. A method for processing a signal in a pulse oximetry device, comprising the steps of:
receiving, at an inlet port of a pulse oximetry device, a time-based signal reflective of one or more optical signals incident on a detector of a pulse oximeter sensor;
using a processor of said pulse oximetry device;
performing a first transform on said time-based signal over a first time window to generate a first transformed signal having at least a frequency component;
performing a second transform on said time-based signal over a second time window to generate a second transformed signal having at least a frequency component, wherein said second time window is disposed within said first time window;
comparing said first and second transformed signals to identify noise components in said first time window;
subtracting said noise components from said first transformed signal to generate a modified transformed signal; and
using said modified transformed signal to generate physiological patient data.

24. The method of claim 23, further comprising:
using said processor for inverse transforming said modified transformed signal to generate a modified time-based signal.

25. The method of claim 24, further comprising:
using said modified time-based signal to identify a blood analyte value.

26. A method for processing a signal in a pulse oximetry device, comprising the steps of:
receiving at an inlet port of a pulse oximetry device, a time-based signal reflective of one or more optical signals incident on a detector of a pulse oximeter sensor;
using a processor of said pulse oximetry device;
performing a first wavelet transform on said time-based signal to generate a first transformed signal having time, frequency and magnitude components;
performing a second wavelet transform on said time-based signal to generate a second transformed signal having time, frequency and magnitude components;
removing at least a first object from one of said first and second transformed signals based on a comparison of said first and second transformed signals to generate a modified transformed signal; and
using said modified transformed signal to generate physiological patient data.

27. The method of claim 26, further comprising:
inverse transforming said modified transformed signal to generate a modified time-based signal that is substantially free of information associated with said first object.

28. The method of claim 27, further comprising:
using said modified time-based signal to identify a blood analyte value.

29. The method of claim 26, wherein said removing step comprises masking at least one duration of one of said first and second transformed signals.

30. The method of claim 29, wherein masking comprises at least one of:
graphically removing a portion of an energy map associated with one of said first and second transformed signals and
numerically removing a duration of one of said first and second transformed signals.

31. The method of claim 26, wherein said removing step comprises:
identifying at least one non-repeating peak in one of said first and second transformed signals ; and
subtracting information associated with said non-repeating peak from one of said first and second transformed signals.

32. A method for processing a signal in pulse oximetry device, comprising the steps of:
receiving, at an inlet port of a pulse oximetry device, a time-based signal reflective of one or more optical signals incident on a detector of a pulse oximeter sensor;
using a processor of said pulse oximetry device:
performing a first wavelet transform on a first portion of said time-based signal, wherein said first wavelet transform utilizes a narrow time window to fit peaks within said time-based-signal;
performing a second wavelet transform on a second portion of said time-based signal, wherein said second wavelet utilizes a wide time window, wherein said wide time window spans at least first and second peaks in said time-based signal;
comparing results of said first and second wavelet transforms to identify transient events in said time-based signal;
generating an output substantially free of said transient events.

33. An apparatus for processing a signal in pulse oximetry, comprising:
a port for receiving an electronic signal reflective of one or more optical signals incident on a detector of a pulse oximeter;
a transformer for first transforming said electric signal for a first time window to generate a first transformed signal and for second transforming said electric signal for a second time window to generate a second transformed signal;
a processor operative to:
compare said first and second transformed signals to identify one or more noise components in at least said first time window;
subtract said one or more noise components from said first transformed signal to generate a modified transformed signal; and
use said modified transformed signal to generate physiological patient data.

34. An apparatus as set forth in claim 33, wherein said port comprises input structure associated with a digital signal processing unit.

35. An apparatus as set forth in claim 33, wherein said transformer comprises a wavelet transformer for applying wavelet transforms to said first and second time windows.

36. An apparatus as set forth in claim 35, wherein said wavelet transformer is operative to apply first and second different wavelet transforms to said first and second time windows, respectively.

* * * * *

UNITED STATES PATENT AND TRADEMARK OFFICE
CERTIFICATE OF CORRECTION

| | | |
|---|---|---|
| PATENT NO. | : 7,515,949 B2 | Page 1 of 1 |
| APPLICATION NO. | : 11/170181 | |
| DATED | : April 7, 2009 | |
| INVENTOR(S) | : Norris | |

It is certified that error appears in the above-identified patent and that said Letters Patent is hereby corrected as shown below:

Column 11, line 61, delete "wave1et", and insert therefor --wavelet--.

Signed and Sealed this

Twelfth Day of May, 2009

JOHN DOLL
*Acting Director of the United States Patent and Trademark Office*